United States Patent
Webster, Jr. et al.

(10) Patent No.: US 7,918,851 B2
(45) Date of Patent: Apr. 5, 2011

(54) IRRIGATED TIP CATHETER AND METHOD FOR MANUFACTURING THEREFOR

(75) Inventors: Wilton W. Webster, Jr., Altadena, CA (US); Mario Solis, Glendale, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 592 days.

(21) Appl. No.: 11/058,434

(22) Filed: Feb. 14, 2005

(65) Prior Publication Data

US 2006/0184165 A1    Aug. 17, 2006

(51) Int. Cl.
*A61B 18/14*    (2006.01)
(52) U.S. Cl. .............. 606/41; 606/48; 607/101; 607/105
(58) Field of Classification Search .............. 606/41, 606/48–50; 607/101–105
See application file for complete search history.

(56) References Cited

U.S. PATENT DOCUMENTS

| | | | |
|---|---|---|---|
| 5,423,811 A | | 6/1995 | Imran et al. |
| 5,472,441 A | * | 12/1995 | Edwards et al. ............... 606/41 |
| 5,735,846 A | | 4/1998 | Panescu et al. |
| 5,913,856 A | | 6/1999 | Chia et al. |
| 5,992,418 A | * | 11/1999 | de la Rama et al. ............ 606/41 |
| 6,017,338 A | | 1/2000 | Brucker et al. |
| 6,056,745 A | * | 5/2000 | Panescu et al. ............... 606/42 |
| 6,120,476 A | * | 9/2000 | Fung et al. ................. 604/95.04 |
| 6,123,699 A | | 9/2000 | Webster, Jr. |
| 6,171,275 B1 | * | 1/2001 | Webster, Jr. ................... 604/20 |
| 6,332,881 B1 | | 12/2001 | Carner et al. |
| 6,405,078 B1 | * | 6/2002 | Moaddeb et al. ............... 604/21 |
| 6,458,123 B1 | | 10/2002 | Brucker et al. |
| 6,522,930 B1 | | 2/2003 | Schaer et al. |
| 6,569,114 B2 | | 5/2003 | Ponzi et al. |
| 6,602,242 B1 | | 8/2003 | Fung et al. |
| 6,611,699 B2 | | 8/2003 | Messing |
| 6,662,034 B2 | * | 12/2003 | Segner et al. ................. 600/373 |
| 2004/0267106 A1 | | 12/2004 | Segner et al. |

* cited by examiner

*Primary Examiner* — Michael Peffley
(74) *Attorney, Agent, or Firm* — Christie, Parker & Hale, LLP

(57) ABSTRACT

An irrigated tip electrode design includes a shell generally surrounding a plug which jointly define a chamber that is fed with fluid by a lumen. The fluid is distributed to the outer surface of the tip electrode through fluid passages. The chamber is advantageously isolated from a region of the tip electrode occupied by electrical and/or electromagnetic components in the tip electrode. Lumens occupied by the these components terminate in blind holes that have no communication with the chamber. A method of fabricating includes providing a shell configured from a rod to provide an open interior cavity, sealing and partially filling the cavity with a plug to form a chamber, then forming fluid passages between the cavity and an outer surface of the tip electrode, and providing a lumen through which fluid can enter the chamber and exit therefrom through the fluid passages.

18 Claims, 7 Drawing Sheets

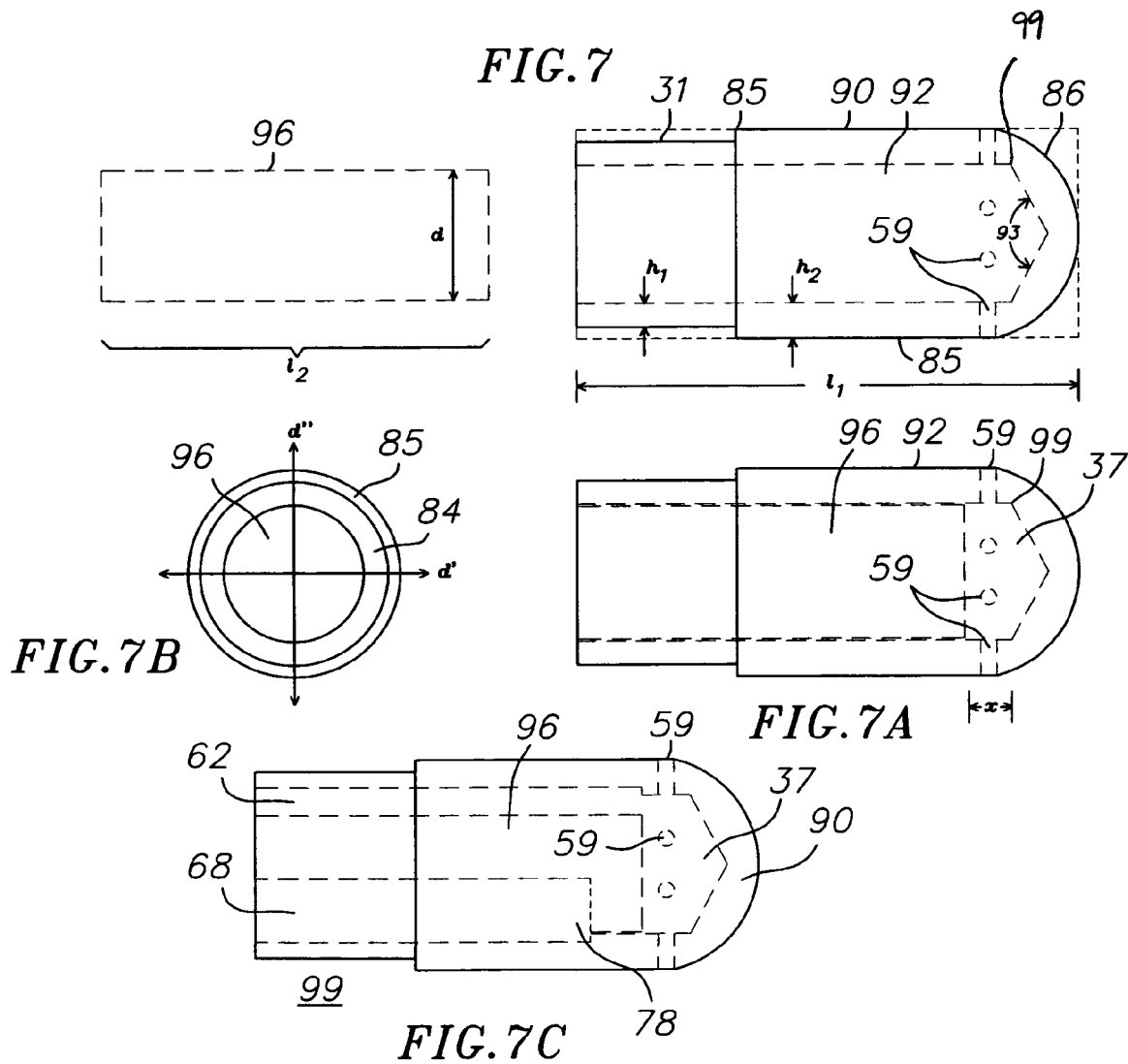

IRRIGATED TIP CATHETER AND METHOD FOR MANUFACTURING THEREFOR

FIELD OF INVENTION

The present invention relates to improved steerable electrode catheters having an irrigated tip, and methods of manufacturing the same.

BACKGROUND OF INVENTION

Electrode physiology catheters applying radio frequency energy ablation have been used to treat heart arrhythmias caused by aberrant electrical activity in the heart tissue. In particular, the catheters are configured with tip electrodes that deliver RF energy to the heart tissue to heat and kill it by ablation. The scarred tissue no longer conducts the errant excitation waves and effectively isolates these waves from other areas in the heart.

For tissue ablation, there are several motivations to deliver the RF energy through the catheter tip, including i) the natural tendency for the tip of the catheter to contact the wall of the heart chamber, ii) the physician's ability to manipulate the tip to the desired location and hold it in place with sufficient pressure to facilitate both stability and RF current flow to the tissue, and iii) the desire to afford sufficient surface area for tip/tissue interface cooling by blood flow around the tip electrode to avoid cutting or charring the tissue. Given the foregoing factors, the tip electrode of the catheter is often the instrument of choice for RF ablation.

Irrigated tip electrode catheters are a known improvement for their ability to cool the tip/tissue interface and/or dilute the adjacent blood by irrigation. Such catheters are configured to emit a cooling liquid, such as normal saline or dextrose/saline solution, out tiny holes in the tip electrode at or near the tip/tissue interface. The liquid cools the tip tissue interface and lowers the adjacent "hematacrit," both of which in turn greatly reduce thrombus formation and charring at the interface.

The design of hole patterns can be crucial for efficient irrigation, that is, the achievement of sufficient cooling without seriously loading the patient with coolant. With proper design of the hole patterns, it is possible to achieve efficient irrigation with insignificant local blood dilution. Accordingly, it is possible to achieve a much improved RF lesion with greatly reduced danger of thrombus formation from charring.

However, a challenge with irrigated tip electrodes is the need to isolate the irrigation liquid from the electrical components attached to and imbedded in the tip electrode, which can include the lead wires, electrical or electromagnetic sensors and/or temperature sensors. A further compounding challenge is the spatial confinement in the tip region which mandates efficient use of the limited space to house the above components. The fabrication of the irrigated tip electrode therefore involves multiple factors, including combining irrigation control for maximum cooling efficiency, sealing off irrigation components from the electrical components, providing sufficient space in the tip electrode for all these components, and avoiding detachment of the tip electrode from the catheter.

It is therefore desirable to provide a catheter with efficient and effective irrigation such as where irrigation holes are situated around the extreme distal end of the tip electrode and the irrigation paths in the tip electrode are of generally equal and short lengths. It is further desirable that such a catheter provides for separate and isolated compartments between the irrigation and electrical components. It is also desirable to provide a method of fabricating such a catheter where there is irrigation control for maximum cooling efficiency, the irrigation is sealed off from the electrical components, there is sufficient space to house all the irrigation and electrical components and/or the tip electrode is securely attached to the catheter.

SUMMARY OF THE INVENTION

The present invention provides an irrigated tip for attachment to an ablation catheter, and a method of manufacture therefor. The irrigated tip electrode has a shell and a plug which jointly define a chamber that is fed by an irrigation lumen. In particular, the shell is configured with an interior cavity that is sealed and partially filled by the plug whose distal end is proximal of the distal end of the interior cavity to define a plenum chamber in the tip electrode. An irrigation lumen is configured in the tip electrode to supply the plenum chamber with irrigation fluid that is then distributed to the outer surface of the tip electrode through fluid passages.

A detailed embodiment of the present invention, an irrigated tip catheter has a catheter body, a control handle and a deflectable tip section. In particular, the catheter body has a proximal end and a distal end and the control handle is at the proximal end of the catheter body. The tip section is at the distal end of the catheter body and comprises a tip electrode having a shell and a plug that jointly define a sealed chamber which receives through a lumen fluid that is distributed through fluid passages to outside of the tip electrode. The chamber is advantageously isolated from a region of the tip electrode occupied by electrical and/or electromagnetic components in the tip electrode. In particular, lumens occupied by the these components terminate in blind holes that have no communication with the chamber.

The present invention also includes a method of fabricating an irrigated tip electrode. One method comprises providing a shell configured from a rod to provide an open interior cavity, forming fluid passages between the cavity and an outer surface of the tip electrode, sealing and partially filling the cavity with a plug to form a chamber, and providing a lumen through which fluid can enter the chamber and exit therefrom through the fluid passages.

In a more detailed embodiment, the method includes drilling of the rod to form the shell and press-fitting the plug into the shell to form a generally monolithic structure. The method may also include drilling the monolithic structure to form an irrigation lumen, where such drilling can occur at or near an interface between the plug and the shell.

In another more detailed embodiment, the method may include inserting the plug into the interior cavity until a proximal end of the plug is flush with a proximal end of the shell, and forming at least one additional lumen in the monolithic structure whose distal end is proximal of the plenum chamber. Moreover, the at least one additional lumen may be devoid of communication with the irrigation lumen and the plenum chamber within the tip electrode.

BRIEF DESCRIPTION OF THE DRAWINGS

These and other features and advantages of the present invention will be better understood by reference to the following detailed description when considered in conjunction with the accompanying drawings wherein:

FIG. 3A is an opposite side cross-sectional view of the catheter tip section of FIG. 3.

FIG. 7 is side view of a shell and a plug prior to placement of the plug in the shell in forming the tip electrode in one embodiment.

FIG. 7A is a side view of the shell and the plug of FIG. 7 after placement of the plug in the shell.

FIG. 7B is an end view of the shell and plug of FIG. 7A.

FIG. 7C is a side view of the shell and the plug of FIG. 7B with lumens drilled.

DETAILED DESCRIPTION OF THE INVENTION

In an embodiment of the invention, there is provided a steerable bi-directional catheter having an irrigated tip. As shown in FIGS. 1-7, catheter 10 comprises an elongated catheter body 12 having proximal and distal ends, a deflectable tip section 14 at the distal end of the catheter body 12, and a control handle 16 at the proximal end of the catheter body 12.

Figure 1:
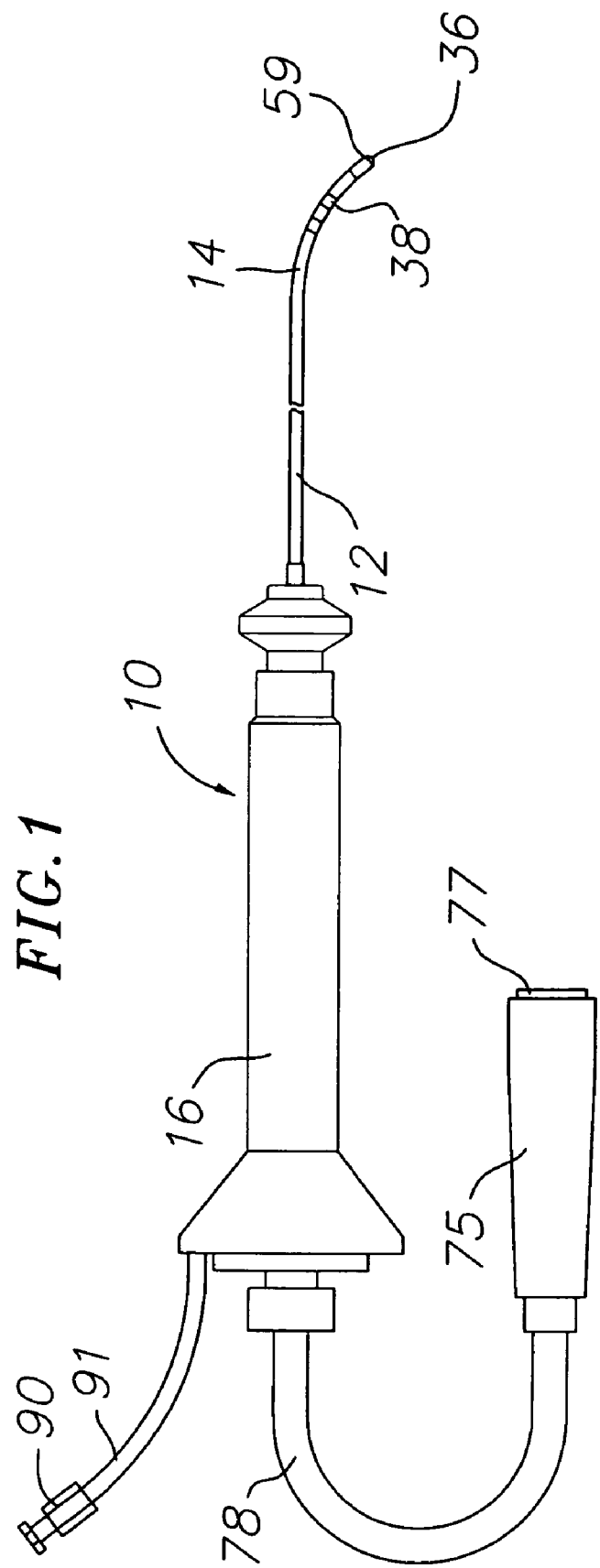
FIG. 1 is a side view of a catheter according to an embodiment of the invention.
Figure 2:
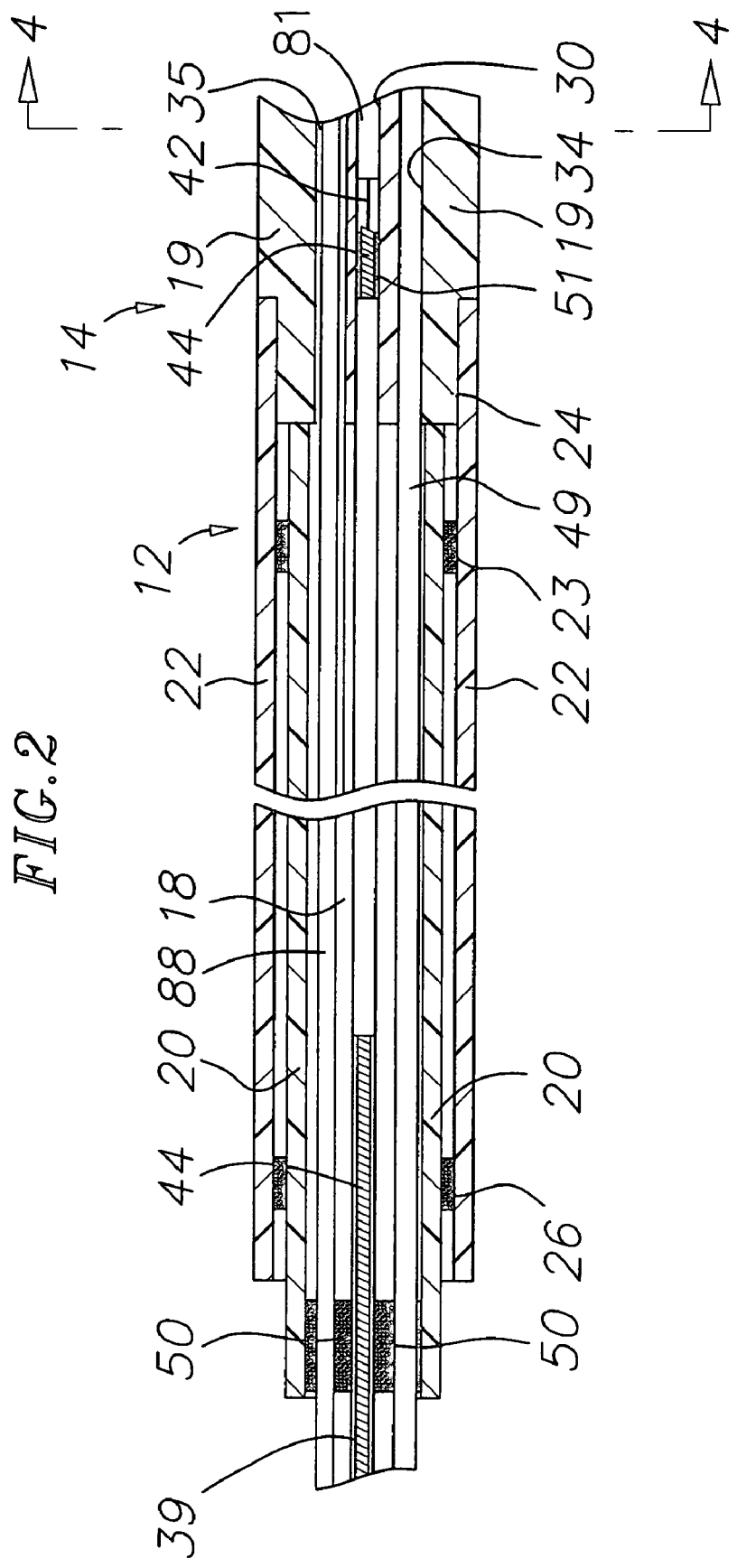
FIG. 2 is a side cross-sectional view of a catheter body according to the invention, including the junction between the catheter body and tip section. It is noted that the first, third and fourth lumens of the tip section are shown in a single representational cross sectional view in order to facilitate the discussion herein. However, it will be understood by one of ordinary skill in the art that no single plane intersects all the lumens shown.

With reference to FIGS. 1 and 2, the catheter body 12 comprises an elongated tubular construction having a single, axial or central lumen 18. The catheter body 12 is flexible, i.e., bendable but with substantially torsional stiffness. The catheter body 12 can be of any suitable construction and made of any suitable material. A presently preferred construction comprises an outer wall 22 made of a polyurethane or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

Extending through the single lumen 18 of the catheter body 12 are lead wires, an infusion tube, a first compression coil through which a first puller wire extends for uni-directional deflection, if not also a second compression coil through which a second puller wire extends for bidirectional deflection. A single lumen catheter body is often preferred over a multi-lumen body because it has been found that the single lumen body permits better tip control when rotating the catheter. The single lumen permits the lead wires, infusion tube, and the puller wire(s) each surrounded by the compression coil(s) to float freely within the catheter body. If such wires and tube were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate an infusion tube, at least one puller wire, lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

An embodiment of the catheter has the outer wall 22 with an outer diameter of from about 0.090 inch to about 0.094 inch and an inner diameter of from about 0.061 inch to about 0.065 inch and the polyimide stiffening tube 20 having an outer diameter of from about 0.060 inch to about 0.064 inch and an inner diameter of from about 0.051 inch to about 0.056 inch.

At least one puller wire 42 for deflecting the tip section 14 extends through the catheter body 12, is anchored at its proximal end to the control handle 16, and is anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 is situated within the catheter body 12 in surrounding relation to the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. Teflon® coating on the puller wire 42 allows it to slide freely within the compression coil 44. If desired, particularly if electrode lead wires are not enclosed by a protective sheath, the outer surface of the compression coil 44 can be covered by a flexible, non-conductive sheath 39, e.g., made of polyimide tubing, to prevent contact between the compression coil 44 and any other wires within the catheter body 12.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

A suitable means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue® Thereafter a second glue joint 26 is formed between the proximal ends of the stiffening tube 20 and outer wall 22 using a slower drying but more permanent glue, e.g., polyurethane.

If desired, a spacer can be located within the catheter body between the distal end of the stiffening tube and the proximal end of the tip section. The spacer provides a transition in flexibility at the junction of the catheter body and tip section, which allows this junction to bend smoothly without folding or kinking. A catheter having such a spacer is described in U.S. patent application Ser. No. 08/924,616, entitled "Steerable Direct Myocardial Revascularization Catheter", the disclosure of which is incorporated herein by reference.

Figure 3:
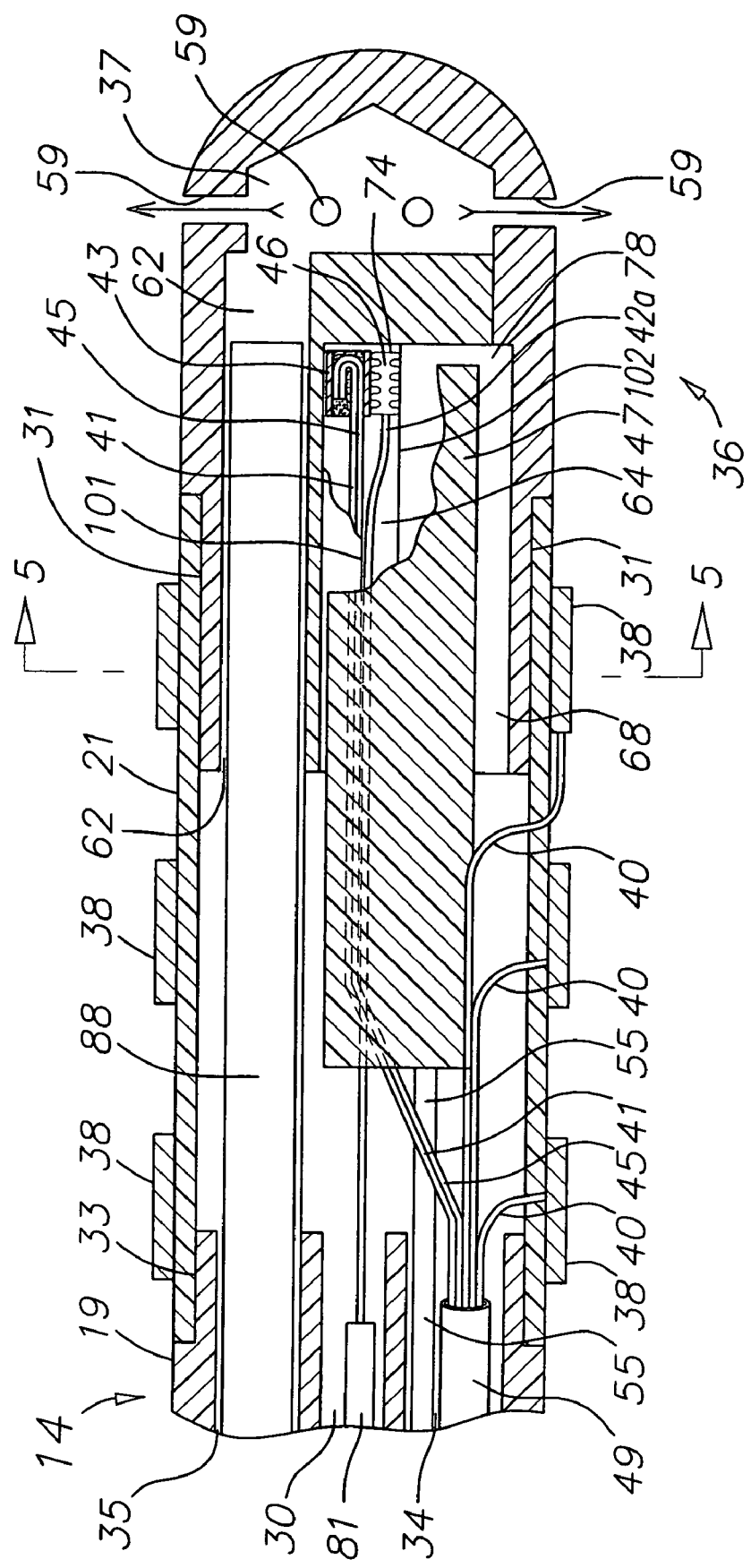
FIG. 3 is a side cross-sectional view of a catheter tip section showing an embodiment of an irrigated tip electrode.
Figure 4:
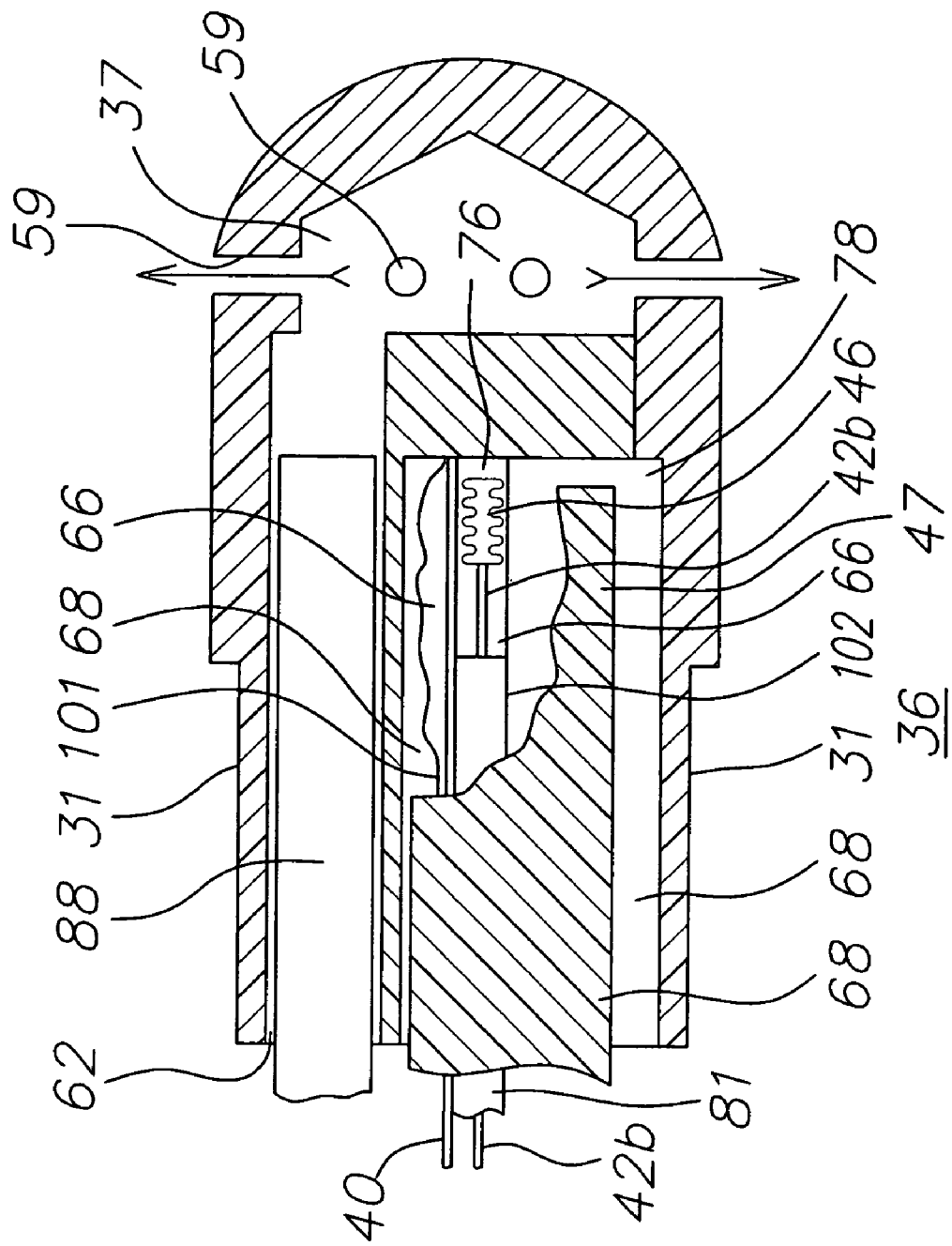
FIG. 4 is a cross-sectional view of the tip section of FIG. 2 taken along line 4-4.

As shown in FIGS. 3, 3A and 4, the tip section 14 comprises a tip electrode 36, and a short section of tubing 19 having multiple off-axis lumens, e.g., three or four or more lumens. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like, but the tubing 19 can comprise a plastic core, an inner plastic layer surrounding the core, a braided stainless steel mesh surrounding the inner layer, and an outer plastic layer surrounding the braided mesh. A suitable tubing is described in U.S. Pat. No. 6,569,114.

The outer diameter of the tip section 14, like that of the catheter body 12, is preferably no greater than about 8 french, more preferably 7 french. The size of the lumens is not critical. In one embodiment, the tip section 14 has an outer diameter of about 7 french (0.092 inch) and the tubing 19 contains four lumens. The diameters of a first lumen 30 and a second lumen 32 are similar in size, and are each preferably 0.018 inch. The diameters of a third lumen 34 and a lumen 35 are also similar in size and are each preferably 0.029 inch.

Carried on the tip section 14 are ring electrodes 38 whose lead wires 40 extend through the third lumen 34 of the tip section, and a thermocouple whose wires 41 and 45 (one of which can serve as the tip electrode lead wire in an alternative embodiment) also extend through the third lumen 34. The tip section 14 also carries an electromagnetic navigation sensor 47 that is generally located in the tip electrode 36. A cable 55 for the sensor 47 extends from the sensor 47 through the lumen 34. A nonconducting sheath 49 can be provided in the lumen 34 for isolating and insulating the wires 40, 41 and 45. Extending through the fourth lumen 35 of the tip section 14 is an infusion tube 88 extending from the control handle 16 and catheter body 12 and into the tip electrode 36.

Extending through the first and second lumens 30 and 32 are puller wires 42a and 42b, respectively, for bidirectional deflection of the tip section 14. Each puller wire has its respective plastic, preferably Teflon®, sheath 81, which prevents the puller wire from cutting into the wall of the tip section 14 when the tip section is deflected.

As shown in the embodiment of FIGS. 3 and 3A, the tip electrode 36 is connected to the tubing 19 of the tip section 14 by means of a plastic housing 21, preferably made of polyetheretherketone (PEEK). The proximal end of the tip electrode 36 is notched circumferentially to form a neck 31, which fits inside the distal end of the plastic housing 21 and is bonded to the housing 21 by polyurethane glue or the like. As discussed further below, the wires, cable and irrigation tube that extend into the tip electrode 36 help keep the tip electrode in place on the tip section.

The proximal end of the plastic housing 21 is bonded with polyurethane glue or the like to the distal end of the tubing 19 of the tip section 14. The distal end of the tubing 19 is notched circumferentially to form a stem 33 which fits inside the proximal end of the housing 21. The plastic housing can be about 1 cm long and the tip electrode 36 can have a diameter about the same as the outer diameter of the tubing 19 and housing 21.

In accordance with a feature of the present invention, the tip electrode 36 has multiple off-axis lumens. In the illustrated embodiment, there are a first lumen 64, a second lumen 66, a third lumen 68 and a fourth lumen 62. The first, second and third lumens terminate in respective blind holes 74, 76 and 78. The fourth lumen 62 however extends through and into a plenum chamber 37 provided in the distal end of the tip electrode. Significantly, the lumens 64, 66, 68 and the blind holes 74, 76, 78 are isolated and spatially separated from the plenum chamber and are as shown in the illustrations proximal of the plenum chamber. Thus, fluid entering and occupying the plenum chamber has no communication with these lumens or holes or, more importantly, the components received therein. Moreover, the relative distal and proximal orientation of the chamber and these components efficiently utilizes the limited space in the tip electrode without compromising their function or operation.

The plenum chamber is in communication with the outer surface of the tip electrode 36 via multiple fluid passages 59 that extend radially from the plenum chamber. The plenum chamber advantageously occupies most if not all of the cross-section of the distal end of the tip electrode 36 such that the travel path of each fluid passage 59 through the distal end of the tip electrode is generally short and generally equal. As such, the irrigation fluid is evenly distributed from the plenum chamber to the outer surface of the tip electrode despite the relatively small hole size or cross section of the fluid passages which may be about 0.010 inch to 0.016 inch in diameter. There may be at least four, and more preferably, at least six fluid passages 59 in the tip electrode. However, it is understood by one of ordinary skill in the art that the number and configuration of the fluid passages can be varied as desired or appropriate.

To supply the fluid to the plenum chamber, the infusion tube 88 extends through the central lumen 18 of the catheter body 12, the fourth lumen 35 of the tip section 14 and the lumen 62 of the tip electrode. The distal end of the tube 88 can be proximal of the plenum chamber or it can extend into the plenum chamber 37. The infusion tube 88 is anchored in the lumen 62 by polyurethane glue or the like. The fluid transported can be used for infusing fluids, e.g., saline, to cool the tip electrode 36, in particular, the tip/tissue interface during ablation. The tip electrode may also be configured to infuse drugs or to collect tissue or fluid samples. The infusion tube may be made of any suitable material, and is preferably made of polyimide tubing. A preferred infusion tube has an outer diameter of from about 0.032 inch to about 0.036 inch and an inner diameter of from about 0.028 inch to about 0.032 inch.

Figure 5:
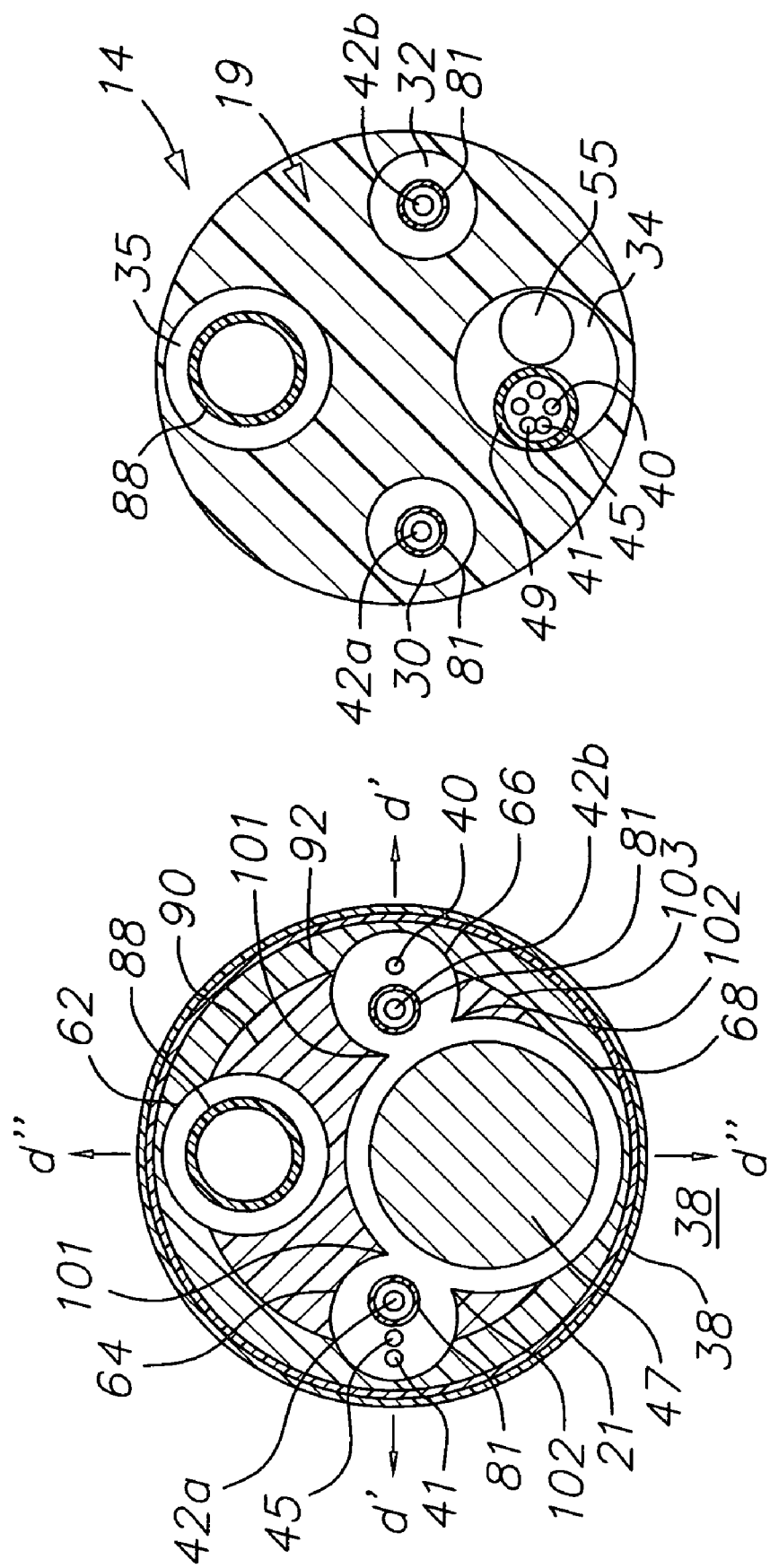
FIG. 5 is a cross-sectional view of the tip electrode of FIG. 3 taken along line 5-5.

As better shown in FIG. 5, the lumens 62 and 68 are generally aligned along one diameter d" of the tip electrode and the lumens 64 and 66 are generally aligned along another diameter d' orthogonal to the diameter d". Described differently, the lumens 62 and 64 occupy a first pair of opposing quadrants and the lumens 66 and 68 occupy a second pair of opposing quadrants. Moreover, the lumens of the tip electrode 36 are generally axially aligned with the lumens of the tubing 14. In particular, the lumen 62 is generally axially aligned with the lumen 35, the lumen 64 with the lumen 30, the lumen 66 with the lumen 32, and the lumen 68 and the lumen 34.

A preferred tip electrode 36 has an effective length, i.e., from its distal end to the distal end of the housing 21, ranging between about 3.0 to 5.0 mm, and an actual length, i.e., from its distal end to its proximal end, of about 4.0 to 6.0 mm.

In the embodiment shown, the three ring electrodes 38 are mounted on the housing 21. It is understood that the presence and number of ring electrodes 38 may vary as desired and such additional ring electrodes 38 can be mounted on the tubing 19. Each ring electrode 38 is slid over the housing 21 and/or the tubing 19 and fixed in place by glue or the like.

The tip electrode 36 can be made of any suitable material, and are preferably machined from platinum-iridium bar (90% platinum/10% iridium). The tip electrode 36 and ring electrodes 38 are each connected to a separate lead wire 40. The lead wires 40 extend through the third lumen 34 of tip section 14, the central lumen 18 of the catheter body 12, and the control handle 16, and terminate at their proximal end in an input jack (not shown) that may be plugged into an appropriate monitor (not shown). As mentioned, the portion of the lead wires 40 extending through the proximal end of the tip section 14, the central lumen 18 of the catheter body 12 and the control handle 16 are enclosed within a protective sheath 49, which can be made of any suitable material, preferably polyimide. The protective sheath 49 is anchored at its distal end to the proximal end of the tip section 14 by gluing it in the third lumen 34 with polyurethane glue or the like.

The lead wires 40 and the ring electrodes 38 are attached to the tip section 14 by any conventional technique. Connection of a lead wire to the tip electrode 36 is accomplished, for example, by welding the lead wire 40 into the hole 76 in the tip electrode 36 (see FIG. 3A which shows the tip electrode without the housing 21, the tubing 19 or the ring electrode 38). Connection of a lead wire 40 to a ring electrode 38 is preferably accomplished by first making a small hole through the tubing 19 and/or the housing 21 (FIG. 3). Such a hole can be created, for example, by inserting a needle through the tubing 19 and/or housing 21 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

The temperature sensing means provided in the tip section 14 may also be a thermistor such as Model No. AB6N2-GC14KA143E/37C sold by Thermometrics (New Jersey). In the thermocouple however of the illustrated embodiment of FIG. 3, the wire 41 is a number "40" copper wire, and the wire 45 is a number "40" constantan wire, which gives support and strength to the wire pair. The wires 41 and 45 of the wire pair are electrically isolated from each other except at their distal ends where they contact and are twisted together, covered with a short piece of plastic tubing 43, e.g., polyimide, and covered with epoxy. The plastic tubing 43 is then attached in the blind hole 74 of the tip electrode 36, by polyurethane glue or the like. The wires 41 and 45 then extend out through the control handle 16 and to a connector (not shown) connectable to a temperature monitor (not shown).

The lead wires 40 and the thermocouple wires 41 and 45 extend through the nonconductive covering 49 that extends also through the lumen 34 of the tubing 19 as mentioned above and through the housing 21 where the distal end of the lead wires are connected to their respective ring electrodes 38 and to the tip electrode 36.

The puller wire 42a extends from the lumen 30 in the tubing 19, through the housing 21 and into the lumen 64 of the tip electrode 36 and is anchored at its distal end in the blind hole 74. Similarly, the puller wire 42b extends from the lumen 32 in the tubing 19, through the housing 21 and into the lumen 66 of the tip electrode and is anchored at its distal end in the blind hole 76. A preferred method for anchoring the puller wires within the blind holes is by crimping metal tubing 46 of hypodermic stock to the distal end of the puller wire 42 and soldering the metal tubing 46 inside the blind holes. Anchoring the puller wires 42 within the tip electrode 36 provides additional support, reducing the likelihood that the tip electrode 36 will fall off the tip section 14. Alternatively, one or both of the puller wires 42 can be attached to the side of the tip section 14.

The cable 55 for the electromagnetic navigation sensor 47 extends through the lumen 34 of the tubing 19, and through the housing 21, its distal end connected to the sensor 47. The sensor 72 is fixedly attached within the tip electrode 36 and the plastic housing 21 by polyurethane glue or the like.

Referring to FIG. 1, the proximal end of the cable 55 extends out the proximal end of the control handle 16 within an umbilical cord 78 to a sensor control module 75 that houses a circuit board (not shown). The cable 55 comprises multiple wires encased within a plastic covered sheath. In the sensor control module 75, the wires of the electromagnetic sensor cable 55 are connected to the circuit board which amplifies the signal received from the electromagnetic sensor 47 and transmits it to a computer (not shown) in a form understandable by the computer The proximal end of the first infusion tube 88 extends through the control handle 16 and terminates in a luer hub 90 or the like at a location proximal to the control handle. In practice, fluid may be injected into the infusion tube 88 through the luer hub 90 (FIG. 1), and flows through the infusion tube 88, through the fourth lumen 35 and through the lumen 62, into the plenum chamber 37 and out the fluid passages 59 in the tip electrode. Again, the fluid passage may have other configurations as desired. For example, the fluid passages 59 may include a longitudinal hole that extends out the distal end of the tip electrode 36, or the tip electrode 36 may be porous enough to allow fluids to pass to the outer surface of the tip electrode, the interconnecting pores forming the fluid passage.

Figure 6:
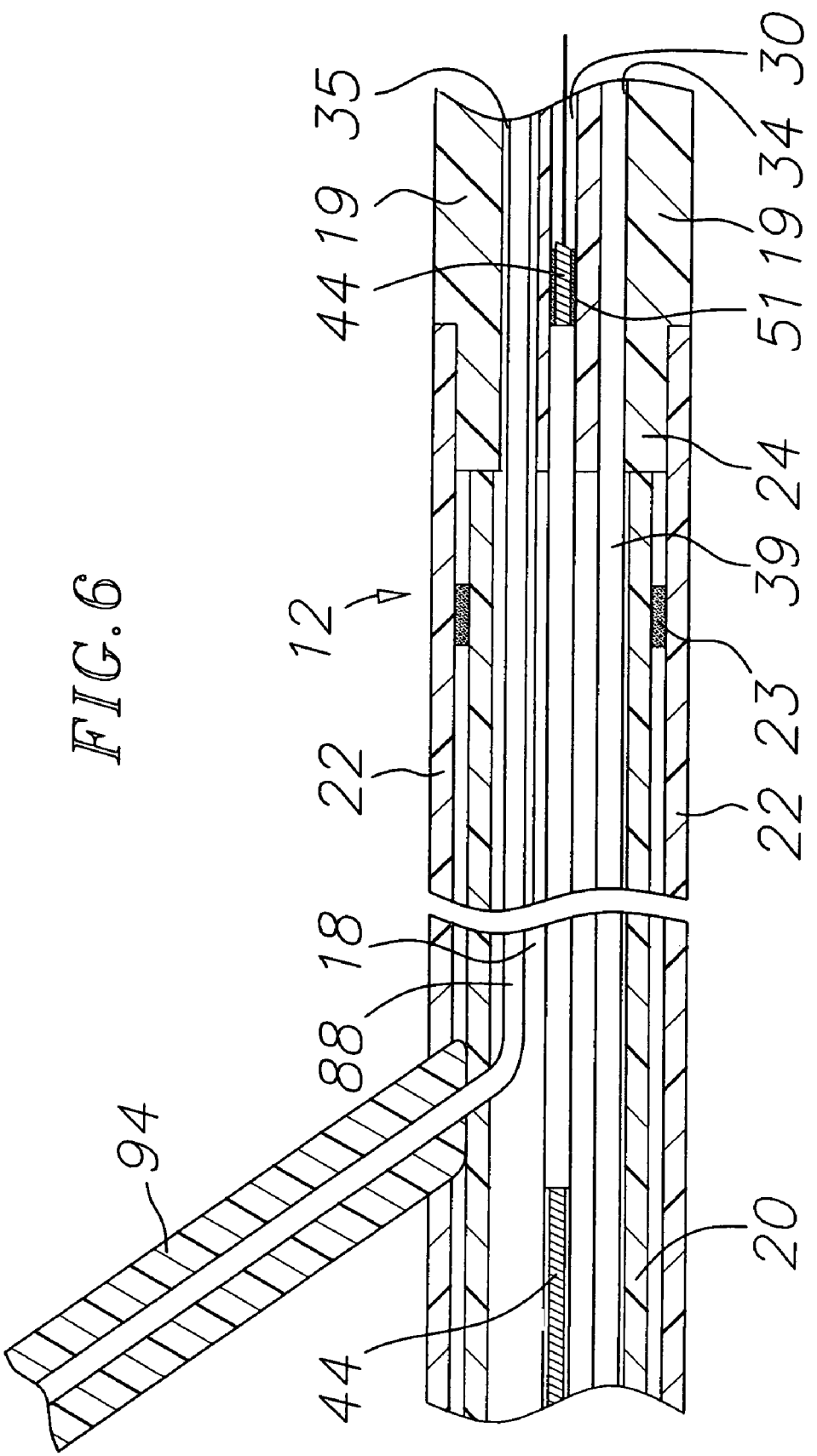
FIG. 6 is a side cross-sectional view of an alternative embodiment of a catheter body according to the invention having a side arm. It is again noted that the first, third and fourth lumens of the tip section are shown in a single representational cross sectional view in order to facilitate the discussion herein. However, it will be understood by one of ordinary skill in the art that no single plane intersects all the lumens shown.

In an alternative arrangement, as shown in FIG. 6, a single lumen side arm 94 is fluidly connected to the central lumen 18 near the proximal end of the catheter body 12. The infusion tube 88 extends through the catheter body 12 and out the side arm 94, where it terminates in a luer hub 90 (FIG. 1) or the like. The side arm 94 is preferably made of the same material as the outer wall 22, but preferably has a greater thickness, e.g., 0.055 inch. Where the side arm 94 meets the catheter body 12, a molded joint can be provided to provide additional strength and support The molded joint can be made of any suitable biocompatable material, and is preferably made of polyurethane.

The lumens 30 and 32 of the tubing 19 in the tip section receiving the puller wires 42a and 42b, respectively, may be in adjacent quadrants, but are preferably in opposing quadrants as illustrated. If desired, the distal ends of one or both of the puller wires may be anchored to the side wall of the catheter tip section for example as, described in U.S. patent application Ser. No. 08/924,611, now U.S. Pat. No. 6,123,699, the entire disclosure of which is incorporated herein by reference. Moreover, the first puller wire may be anchored proximal to the anchor location of the second puller wire.

A catheter construction comprising multiple puller wires including control handle construction is disclosed in U.S. patent application Ser. No. 08/924,611, Entitled "Omni-Directional Steerable Catheter", the entire disclosure of which is incorporated herein by reference. Such application describes a suitable control handle for manipulating two or more puller wires. Other suitable control handles are disclosed in U.S. Pat. No. 6,602,242, the entire disclosure of which is incorporated herein.

In accordance with a feature of the invention, the tip electrode is attached to the tip section through multiple attachment means. In the illustrated embodiment, the attachment means and structures include at least the infusion tube, and the puller wires, if not also the wire of the navigation sensor, to provide at least three if not four structure or points of attachment, each of which extends between the tubing 19 and the tip electrode 38. To that end, the hypodermic stock anchoring the distal end of the puller wires can be of a greater length, e.g., at least 3.0 mm, preferably ranging between 3.0 mm and 4.0 mm for greater anchoring capabilities to the tip electrode. In any case, these generally tensile structures of attachment can remain even if the housing 21 is absent in the instance the tubing 19 and the tip electrode 36 are attached directly to each other or indirectly by or through another component.

FIG. 7 illustrates the tip electrode 36 in an initial process of manufacture. The tip electrode 36 is configured from a first rod 82 which is notched circumferentially at its proximal end to form the neck 31 (see also FIGS. 3 and 3A) and a body 85. The distal end of the body 85 is milled to form an atraumatic end 86, e.g., a generally rounded conical shape. The interior of the rod is then drilled to form a shell 90 with predetermined thicknesses h1 around the neck and h2 around the body and a depth or length L1 defining an open interior cavity 92. The cavity 92 has a generally cylindrical proximal portion with a predefined length and diameter, and a generally conical or half-spherical distal portion. The conical distal portion may have a distal conical tip cross-section 93 spanning about 118 degrees. The rod may be constructed of any suitable material with sufficient structural strength and/or electrical conductivity, and is preferably of a noble metal alloy, for example 90/10 PT/IR.

Formed of the same or comparable material of which the shell is formed, a second rod or plug 96 has a generally elongated configuration with a generally circular cross-section. The plug 96 having a diameter d suitable for a press fit into the interior cavity 92 is inserted into the shell 90 to seal and partially fill the cavity. To that end, although the predetermined diameter d is generally equal or slightly larger than the predetermined diameter of the interior cavity, the plug has a predetermined length L2 that is lesser than the predetermined length L1 of the shell 90. As such, when the plug is inserted into the shell (see FIG. 7A), the plug can be positioned relative to the shell with its proximal end flush with the proximal end of the shell while its distal end is proximal of an edge location 99 by a predetermined distance X equaling at least about three times the diameter of the fluid passage 59. As such, the depth of the plenum chamber (from the distal end of the plug 96 to the distal end of the plenum chamber) is advantageously minimal compared to the length of the shell, which maximizes the region in the tip electrode proximal the plenum chamber for housing other components in the tip electrode.

It is understood by one of ordinary skill in the art that the proximal ends of the shell and the plug need not be flush if that is not a consideration for drilling of the lumens and blind holes in the tip electrode described further below. In any case, the press fit between the rod 96 and the shell 90 forms a fluid-tight seal such that the plenum chamber 37 and the lumen 62 opening into the plenum chamber are sealed from electrical components and any potting compound and solder that may be used in the tip electrode. In particular, fluid in the plenum chamber is limited to leaving the chamber through only the fluid passages 59 and/or the infusion tube 88 that feeds into the plenum chamber.

The press fit also renders the plug and the shell a generally monolithic structure such that drilling can be accomplished on the proximal face of the structure without regard to an interface 103 between the plug and the shell (see FIG. 7B), particularly where the proximal ends of the plug and shell after assembly are flush with each other. Drilling can be initiated at the proximal face toward the distal end to form the lumens 62 and 68 (lumens 66 and 68 not shown) and the blind hole 78 (blind holes 74 and 76 not shown) for receiving the various electrical and nonelectrical components provided the tip electrode. In the illustrated embodiment of FIG. 7B, drilling occurs at four locations generally along two orthogonal diameters d' and d" of the cross section of the structure, forming the lumens 62, 64, 66 and 68. Given the confined space in the tip electrode, the lumens 64 and 66 are shown overlapping or otherwise in communication with the lumen 68, but only to a limited degree such that the function and operation of each lumen and the contents thereof are not adversely affected. That is, the overlap (between longitudinal edges 101 and 102 better shown in FIGS. 3, 3A and 5) is not so large that the respective components of neighboring lumens can significantly commingle or become tangled with each other. It is understood by one of ordinary skill in the art that this need not be so as the lumens can be configured without any overlap.

By situating one or more of the lumens 62, 64, 66, 68 to traverse the interface 103 between the plug and the shell (best seen in FIG. 5), further strength and integrity can be imparted to the interface and bonding between the plug and the shell. As such, space in the tip electrode can be more efficiently utilized where the lumens are drilled after the plug and shell have been assembled. However, it is understood by one of ordinary skill in the art that the plug 96 can be drilled before it is press fitted into the shell 90. In any case, there should be no overlap between the lumen 62 and any of the lumens 62, 64, 68, so that there is no opportunity for the fluid carried in the tube 88 to come in contact with the respective components of the lumens 62, 64, 68.

The fluid passages 59 in the distal end of the shell 90 are formed from laser or electrical discharge machining (EDM) drilling, which can occur from the outer surface of the tip electrode toward the plenum chamber, prior to or after assembly of the plug 96 and shell 92 (although it is generally preferred that the drilling occurs before the plug is inserted so that any drilling debris inside the shell can be more easily removed). To ensure that each fluid passage has substantially the same travel path from the plenum chamber to the outer surface of the tip electrode, the drilling which creates the interior cavity 92 should be conducted in a manner that ensures the thickness of the distal end 86 is generally uniform, such as drilling centrally along the longitudinal axis of the rod 82.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. It is further understood that the drawings are not necessarily to scale.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An irrigated tip catheter comprising:
   a catheter body with a proximal end and a distal end;
   a control handle at the proximal end of the catheter body;
   a tip section at the distal end of the catheter body and comprising a tip electrode having:
      a shell and a plug jointly defining a chamber, the chamber occupying substantially all of a cross-section of a distal end of the tip electrode, wherein the plug is at least partially fitted in the shell such that the chamber is between a distal end of the shell and a distal end of the plug, wherein the distal end of the plug creates a fluid tight seal with the shell;
      at least a first lumen extending through the plug to pass fluid into the chamber, and at least one second lumen off-axis to the first lumen extending through the plug and having a distal end terminating proximal the chamber for carrying electrical and/or electromagnetic components of the tip electrode;
      a plurality of radial fluid passages to pass fluid from the chamber to outside the tip electrode;
      wherein the chamber is isolated from the second lumen and a region of the tip electrode occupied by electrical and/or electromagnetic components in the tip electrode.

2. A catheter of claim 1, wherein the region is proximal the chamber.

3. A catheter of claim 1, further comprising an irrigation tube that extends through the catheter body and the tip section and its distal end is in communication with the chamber.

4. A catheter of claim 1, wherein the components include a navigation sensor.

5. A catheter of claim 1, wherein the components include a temperature sensor.

6. A catheter of claim 1, further comprising attachment means extending between the tip electrode and the tip section.

7. A catheter of claim 6, wherein the attachment means include an irrigation tube.

8. A catheter of claim 6, wherein the attachment means include at least one puller wire.

9. A catheter of claim 7, wherein the attachment means include a lead wire.

10. A catheter of claim 8, wherein the shell and the plug are composed of generally the same material.

11. An irrigated tip electrode adapted for attachment to a catheter, comprising:
    a shell in a generally surrounding relationship with a plug, the shell and plug jointly defining an interior cavity extending between a distal end of the plug and a distal end of the shell, the interior cavity occupying substantially all of a cross-section of a distal end of the shell, and wherein the distal end of the plug creates a fluid tight seal with the shell;
    a plurality of radial fluid passages between the cavity and an outer surface of the distal end of the shell,
    a first lumen extending through the plug and in communication with the cavity to pass fluid into the cavity; and
    at least one additional lumen off-axis to the first lumen extending through the plug and having a distal end proximal of the cavity, the at least one additional lumen being devoid of communication with the first lumen and the cavity within the tip electrode.

12. A tip electrode of claim 11, wherein the shell has a neck adapted for attachment to the catheter.

13. A tip electrode of claim 11, wherein the plug has a diameter generally equal to a diameter of the interior cavity to form a generally monolithic structure with the shell.

14. A tip electrode of claim 11, wherein the first lumen is a drilled lumen.

15. A tip electrode of claim 14, wherein the first lumen crosses an interface between the plug and the shell.

16. A tip electrode of claim 11, wherein a proximal end of the plug is flush with a proximal end of the shell.

17. An irrigated tip electrode, comprising:
    a plug at least partially fitted in a shell to define a distal irrigation chamber between a distal end of the plug and a distal end of the shell, wherein the distal irrigation chamber occupying occupies substantially all of a cross-section of the distal end of the shell, and wherein the distal end of the plug creates a fluid tight seal with the shell;
    an irrigation lumen extending through the plug and having a distal end in communication with the distal irrigation chamber, the irrigation lumen receiving a tube adapted to pass fluid into the distal irrigation chamber;
    a plurality of radial fluid passages from the chamber to a tip/tissue interface of the electrode; and
    at least a first lumen off-axis to the irrigation lumen extending through the plug and having a distal end proximal of the chamber, the first lumen having no communication with either the irrigation lumen or the chamber, the first lumen receiving a component carried by the tip electrode.

18. An irrigated tip electrode of claim 17, wherein the component is selected from the group consisting of navigation sensors, temperature sensors, lead wires, puller wires, cables, and anchor struts.

* * * * *

UNITED STATES PATENT AND TRADEMARK OFFICE
CERTIFICATE OF CORRECTION

| | |
|---|---|
| PATENT NO. | : 7,918,851 B2 |
| APPLICATION NO. | : 11/058434 |
| DATED | : April 5, 2011 |
| INVENTOR(S) | : Wilton W. Webster, Jr. et al. |

Page 1 of 1

It is certified that error appears in the above-identified patent and that said Letters Patent is hereby corrected as shown below:

Column 12, Claim 17, line 38      Delete "occupying"

Signed and Sealed this
Fifteenth Day of November, 2011

David J. Kappos
*Director of the United States Patent and Trademark Office*